(12) United States Patent
Ahmad et al.

(10) Patent No.: US 7,078,177 B2
(45) Date of Patent: Jul. 18, 2006

(54) METHOD OF ASSAYING FOR AGONISTS OR ANTAGONIST OF DYNORPHIN A BINDING TO THE MAS RECEPTOR

(75) Inventors: Sultan Ahmad, St-Laurent (CA); Eric Grazzini, St-Laurent (CA); Paola Lembo, St-Laurent (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/250,629

(22) PCT Filed: Dec. 19, 2001

(86) PCT No.: PCT/SE01/02854

§ 371 (c)(1),
(2), (4) Date: Jun. 20, 2003

(87) PCT Pub. No.: WO02/052267

PCT Pub. Date: Jul. 4, 2002

(65) Prior Publication Data

US 2004/0171080 A1    Sep. 2, 2004

Related U.S. Application Data

(60) Provisional application No. 60/257,977, filed on Dec. 22, 2000.

(51) Int. Cl.
  *G01N 33/566*  (2006.01)
  *G01N 33/567*  (2006.01)
  *C07K 14/705*  (2006.01)

(52) U.S. Cl. ................ 435/7.2; 435/7.21; 530/350

(58) Field of Classification Search ........... 435/7.21, 435/69.1, 69.7, 325; 530/302, 350; 436/504; 536/23.5
See application file for complete search history.

(56) References Cited

U.S. PATENT DOCUMENTS 5,017,689 A * 5/1991 Hruby et al. ............... 530/327

FOREIGN PATENT DOCUMENTS

WO    WO 9932519    7/1999

OTHER PUBLICATIONS

Naqvi, et al. Structure-Activity Relationship Studies of Dynorphin A and Related Peptides. Peptides, 1998. 19(7): 1277-1292.*
Ambroz et al. Dec. 3, 1991. The mas oncogene enhances angiotensin-induced [Ca2+]i responses in cells with pre-existing angiotensin II receptors. Biochim Biophys Acta. 1133(1): 107-111.*
Tang et al. Dynorphin A elicits an increase in intracellular calcium in cultured neurons via a non-opioid, non-NMDA mechanism. J Neurophysiol. May 2000; 83(5): 2610-5.*
Young et al. Jul. 1998. Characterization of the rat mas oncogene and its high-level expression in the hippocampus and cerebral cortex of rat brain. Proc Natl Acad Sci USA 85: 5339-5342.*
Selbie et al, 1998. Trends in Pharmacol Sci. 19(3):87-93.*
Kawanabe et al, 2003. Biochemical Pharmacology. 65: 1435-1439.*
Michael Dumont et al., "Interactions of Dynorphin A and Related Peptides with Cardiac Ouabain Binding Sites," J Mol Cell Cardiol, vol. 28, p. 615-621, (1996).
Thomas Walther et al., "Sustained Long Term Potentiation and Anxiety in Mice Lacking the Mas Protooncogene," The Journal of Biological Chemistry, vol. 273 (No. 19), p. 11867-73, (1998).
Oliver Von Bohlen Und Halbach et al., "Interaction Between Mas and the Angiotensin AT1 Receptor in the Amygdala," J. Neurophysiol., vol. 83 (No. 4), p. 2012-2021, (2000).
Mitsuyuki Ichinose et al., "Enhancement of phagocytosis by dynorphin A in mouse peritoneal macrophages," Journal of Neuroimmunology, vol. 60, p. 37-43, (1995).

* cited by examiner

*Primary Examiner*—Brenda Brumback
*Assistant Examiner*—Zachary C. Howard
(74) *Attorney, Agent, or Firm*—Robin S. Quartin

(57) ABSTRACT

The present invention is directed to assays that can be used to screen for compounds that act as agonists or antagonists or inverse agonists of Dynorphin A and its analogues. The assays are based upon the binding of Dynorphin A and its analogues to the rat and human MAS receptors.

4 Claims, No Drawings

METHOD OF ASSAYING FOR AGONISTS OR ANTAGONIST OF DYNORPHIN A BINDING TO THE MAS RECEPTOR

CROSS-REFERENCE TO RELATED APPLICATIONS

This application is the National Stage of International Application No. PCT/SE01/02854, filed Dec. 19, 2001, which claims the benefit under 35 U.S.C. §119(e) of U.S. Provisional Application 60/257,977, filed Dec. 22, 2000.

FIELD OF THE INVENTION

The present invention is directed to assay methods that can be used to determine whether a test compound can be used to modulate the binding and activity of Dynorphin A and analogues at the human MAS receptor. Compounds identified as being effective modulators have potential use as therapeutic agents in treating pain, neuropathic and inflammatory disorders, learning and memory, anxiety disorders as well as the regulation of cardiovascular functions.

BACKGROUND OF THE INVENTION

A. Dynorphin A

Dynorphin was discovered in 1979 as being an endogenously potent opioid peptide (PNAS, USA 76:6666–6670: 1979). The pharmacological actions of dynorphins are quite vast. Dynorphin A and related peptides have been shown to be moderately effective in non-thermal and mechanical analgesia when administered ICV (Dubner, R., Trends Neurosci. 15:96–103, 1992) and have also been used in the clinic for the treatment of intractable pain in cancer patients (Wen, H. L., Central and peripheral endorphins: basic and clinical aspects, New York: Raven Press; 1993:319–323). Dynorphins are also known to have an effect on the cardiovascular system via the central and peripheral nervous systems (Dumont, M. 37:1–33, 1996). Moreover, Dynorphin A has an immunomodulatory activity. When administered to mice, Dynorphin A enhanced phagocytosis in the mouse peritoneal macrophages. This phagocytic activity was not inhibited by naloxone treatment suggesting the involvement of a non-opioid receptor (J. Neuroimmunol. 60:37–43, 1995).

Even though, Dynorphin A was first described as a potent opioid peptide with selectivity for kappa opioid receptor, some of its pathological and physiological actions have been proposed to be mediated by non-opioid receptors. Hence, here we described for the first time that Dynorphin A is able to activate and bind to the MAS receptor.

The human MAS oncogene receptor was first isolated in 1986 via a tumorgenicity assay in nude mice (Young, M., Cell, 45:711–719, 1986). This receptor codes for a seven-transmembrane domain protein and within its coding sequence a hallmark feature is present such as the NPY motif in the seventh transmembrane domain. The MAS receptor is expressed in the ventral nervous system (CNS) with highest signal of the mRNA observed in the hippocampus, cortex, cerebellum, piriform cortex and olfactory bulb. The mRNA for this receptor has also been detected in peripheral tissues including the testis, kidney, and heart (FEBS Letters, 357, 27–32, 1995). The expression of MAS receptor is highly regulated during development and neuronal activity. Interestingly, mice lacking the MAS protooncogene not only displayed an increased anxiety but long-term potentiation was prolonged without affecting the gross morphology of the hippocampus (JBC, 273,11867–11873, 1998).

Hence, drugs targeted at the MAS receptor as agonists, antagonists or inverse agonists could be potentially used for treating problems of long-term memory neuropathic and inflammatory disorders, as well as cardiovascular dysfunction.

B. G Protein-Coupled Receptors

G protein coupled receptors (GPCRs) constitute a family of proteins sharing a common structural organization characterized by an extracellular N-terminal end, seven hydrophobic alpha helices putatively constituting transmembrane domains and an intracellular C-terminal domain. GPCRs bind a wide variety of ligands that trigger intracellular signals through the activation of transducing G proteins (Caron, et al., Rec. Prog. Horm. Res. 48:277–290 (1993); Freedman, et al., Rec. Prog. Horm. Res. 51:319–353 (1996)).

More than 300 GPCRs have been cloned thus far and it is generally assumed that there exist well over 1,000 such receptors. Roughly 50–60% of all clinically relevant drugs act by modulating the functions of various GPCRs (Gudermann, et al., J. Mol. Med. 73:51–63 (1995)). Many of the clinically relevant receptors are located in the central nervous system.

Among the GPCRs that have been identified and cloned is a gene that encodes a protein homologous to the receptors of the DRR/RTA family. We called this receptor MAS receptor and described the structure of the gene as it exists in humans. However, the endogenous ligand for this family of receptors has not previously been identified (Cell: 45, 711–719 1986, JBC 273,11867–11873 1998, WO 99/32519).

SUMMARY OF THE INVENTION

The present invention is based upon the discovery that Dynorphin A and its analogues (Dynorphin A-amide and Dynorphin 1-13) activates the rat and human MAS receptor. Recombinant cells expressing either rat or human MAS receptor can be used in conjunction with Dynorphin A and its analogues in screening assays designed to identify agonists inverse agonists and antagonists. Thus, in its first aspect, the invention is directed to a method of assaying a test compound for its ability to bind to the MAS receptor. This is accomplished by incubating cells or membranes expressing the receptor gene with Dynorphin A and its analogues and test compound. The extent to which the binding of Dynorphin A and its analogues is displaced is then determined. Radioligand assays or enzyme-linked immunosorbent assays may be performed in which either Dynorphin A and its analogues or the test compound is detectably labeled. Although any cell expressing MAS receptor may be used, a recombinant cell expressing a heterologous MAS receptor gene from either the rat or human is preferred. The term "heterologous" as used herein refers to any MAS receptor gene transfected into a cell, i.e., the term refers to any non-endogenous MAS receptor.

The invention also encompasses methods of determining if a test compound is an agonist, antagonist, or inverse agonist of Dynorphin A and its analogues binding based upon a functional assay. One way to carry out such assays is to incubate a cell expressing MAS receptor with the test compound and to then determine whether intracellular phospholipase C, adenyl cyclase activity or intracellular calcium concentrations are modulated. Results should typically be compared with those obtained when incubations are performed in a similar manner but in the absence of test compound. In general, functional assays of this type will be performed in conjunction with binding assays of the sort described above. The preferred cell for use in the assays is a recombinant cell that has been transformed with a MAS receptor gene. Test compounds that act as agonists should produce an increase in phospholipase C, decrease or increase in adenylyl cyclase activity or increase in intracellular levels of calcium. Inverse agonists may reduce phospholipase C activity or intracellular calcium levels, particularly if assays are performed in the presence of a fixed amount of Dynorphin A and its analogues. Antagonists, should block the binding of Dynorphin A and its analogues to the receptor but not produce the opposite response in terms of phospholipase C activity or intracellular calcium that is the hallmark of an inverse agonist.

DETAILED DESCRIPTION OF THE INVENTION

The present invention is directed to assays that can be used to screen compounds for their ability to modulate the binding of Dynorphin A and its analogues to the rat and human MAS receptors. Any form of Dynorphin A and its analogues or fragments may be used (Dynorphin A: YGG-FLRRIRPKLKWDNQ-COOH or NH2(SEQ ID NO:1)). Those peptides may be obtained commercially (e.g Bachem, American Peptide Company) or can be synthesized using standard methodologies well known in the art. The peptide may be detectably labeled with radioisotopes such as $^{125}$I or, alternatively, fluorescent or chemiluminescent labels can be incorporated. Also, the peptide can be joined to enzymes that are readily detectable such as horseradish peroxidase.

The MAS receptor may be cloned from rat and/or human cells/tissues using the procedure described in Young, M., *Cell*, 45:711–719, 1986. The Examples section provides a detailed description of a procedure that may be used in cloning MAS receptor. Once obtained, the MAS receptor sequence should be incorporated into an expression vector with a promoter active in mammalian cells (Sambrook, et al., *Molecular Cloning: A Laboratory Manual*, 2nd Ed., Cold Spring Harbor Press (1989)). Examples of promoters that may be used include that of the mouse metallothionein I gene (Hamer, et al., *J. Mol. Appl. Gen.* 1:273–288 (1982)); the immediate-early and TK promoter of herpes virus (Yao, et al., *J. Virol.* 69:6249–6258 (1995); McKnight, *Cell* 31:355–365 (1982)); the SV 40 early promoter (Benoist, et al., *Nature* 290:304–310 (1981)); and, the CMV promoter (Boshart, et al., *Cell* 41:521–530 (1985)). Vectors may also include enhancers and other regulatory elements.

Once expression vectors have been constructed, they can be introduced into a mammalian cell line by methods such as calcium phosphate precipitation, microinjection, electroporation, liposomal transfer, viral transfer or particle mediated gene transfer. Although other mammalian cells may be used, HEK-293 cells have been found to give successful results and a procedure for expressing MAS receptor in these cells is described in the Examples section. Standard procedures for selecting cells and for assaying them for the expression of MAS receptor (e.g., by Northern analysis) may be performed.

Once the Dynorphin A (or an analogue) peptide and cells expressing the rat and human MAS receptors have been obtained, assays may be performed to determine whether test compounds have any effect on binding. A wide variety of different types of assays can be performed using standard methods well known in the art. For example, in radioligand binding assays, cells expressing MAS receptor are incubated with Dynorphin A and its analogues and with a compound being tested for binding activity. The preferred source of MAS receptor is recombinantly transformed HEK-293 cells. Other cells may also be used provided they do not express other proteins that strongly bind Dynorphin A and its analogues. This can easily be determined by performing binding assays on cells transformed with MAS receptor and comparing the results obtained with those obtained using their non-transformed counterparts.

Assays may be performed using either intact cells or with membranes prepared from the cells (see e.g., Wang, et al., *Proc. Natl. Acad. Sci. U.S.A.* 90:10230–10234 (1993)). As suggested above, the membranes, or cells, are incubated with Dynorphin A and its analogues and with a preparation of the compound being tested. After binding is complete, receptor is separated from the solution containing ligand and test compound, e.g., by filtration, and the amount of binding that has occurred is determined. Preferably, the ligand used is detectably labeled with a radioisotope such as $^{125}$I. However, if desired, other types of labels can also be used. Among the most commonly used fluorescent labeling compounds are fluorescein isothiocyanate, rhodamine, phycoerythrin, phycocyanin, allophycocyanin o-phthalaldehyde and fluorescamine. Useful chemiluminescent compounds include luminol, isoluminol, theromatic of acridinium ester, imidazole, acridinium salt, and oxalate ester.

Nonspecific binding may be determined by carrying out the binding reaction in the presence of a large excess of unlabeled ligand. For example, labelled Dynorphin A and its analogues may be incubated with receptor and test compound in the presence of a thousandfold excess of unlabeled Dynorphin A and/or its analogues. Nonspecific binding should be subtracted from total binding, i.e., binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with receptor when, in fact, binding is being inhibited by some other mechanism. For example, the compound being tested should be in a buffer which does not itself substantially inhibit the binding of Dynorphin A and its analogues and should, preferably, be tested at several different concentrations. Preparations of test compound should also be examined for proteolytic activity and it is desirable that antiproteases be included in assays. Finally, it is highly desirable that compounds identified as displacing the binding of Dynorphin A and its analogues be reexamined in a concentration range sufficient to perform a Scatchard analysis of the results. This type of analysis is well known in the art and can be used for determining the affinity of a test compound for receptor (see e.g., Ausubel, et al., *Current Protocols and Molecular Biology*, 11.2.1–11.2.19 (1993)); *Laboratory Techniques in Biochemistry and Molecular Biology*, Work, et al., Ed. N.Y. (1978)). Computer programs may be used to help in the analysis of results (e.g., Munson, P., *Methods Enzymol.* 92:543–577 (1983)).

Depending upon their effect on the activity of the receptor, agents that inhibit the binding of Dynorphin A and its analogues to receptor may be either agonists or antagonists. Activation of receptor may be monitored using a number of different methods. For example, phospholipase C assays may be performed by growing cells in wells of a microtiter plate and then incubating the wells in the presence or absence of test compound total inositol phosphates (IP) may then be extracted in resin columns, and resuspended in assay buffer. Assay of IP thus recovered can be carried out using any method for determining IP concentration. Typically, phospholipase C assays will be performed separately from binding assays, but it may also be possible to perform binding phospholipase C assays on a single preparation of cells.

Activation of receptor may also be determined based upon a measurement of intracellular calcium concentration. For example, transformed HEK-293 cells may be grown on glass cover slides to confluence. After rinsing, they may be incubated in the presence of an agent such as Fluo-3, Fluo-4 and FURA-2 AM (Molecular Probe F-1221). After rinsing and further incubation, calcium displacement may be measured using a photometer. Other types of assays for determining intracellular calcium concentrations are well known in the art and may also be employed.

Assays that measure the intrinsic activity of the receptor, such as those based upon inositol phosphate measurement, may be used in order to determine the activity of inverse agonists. Unlike antagonists which block the activity of agonists but produce no activity on their own, inverse agonists produce a biological response diametrically opposed to the response produced by an agonist. For example, if an agonist promoted an increase in intracellular calcium, an inverse agonist would decrease intracellular calcium levels.

The radioligand and cell activation assays discussed above provide examples of the types of assays that can be used for determining whether a particular test compound alters the binding of Dynorphin A and its analogues to the human/rat MAS receptors and acts as an agonist or antagonist. There are many variations on these assays that are compatible with the present invention. Such assays may involve the use of labelled antibodies as a means for detecting Dynorphin A and its analogues that has bound to receptor or may take the form of the fluorescent imaging plate reader assay (FLIPR) as described in the Examples section herein.

EXAMPLES

I. Methods
Preparation of Clone Rat and Human MAS Receptor:

See description in: *Cell* 1986 Jun. 6;45(5):711–9

Expression
HEK-293 cells were transfected with a mammalian expression construct coding for the rat and human MAS receptor (pcDNA 3.1 vector, Invitrogen) using the Superfect reagent (Qiagen). A stable receptor pool of MAS receptor was developed by applying a selection marker (G418, 0.9 mg/ml) and the cells were maintained in this selection medium. The presence of mRNA specific for clone MAS receptor was assessed by Northern blot analysis and by the reverse transcriptase polymerase chain reaction (RT-PCR).

Ligands
In order to identify the ligand of clone rat and human MAS receptor, a collection of peptide and non-peptide ligands was obtained from commercial sources (Sigma, CalBiochem, American Peptide Company, Bachem, RBI, Phoenix). The compounds were dissolved in water/DMSO at 3 µM and placed in 96 well microplates. A total of 1000 compounds (peptides and non-peptides) were prepared and tested.

Assays
1) FLIPR Assay
A functional assay was performed with FLIPR (Fluorescent Imaging Plate Reader, Molecular Devices) using the fluorescent calcium indicator Fluo-3 (Molecular Probes) on a 96 well platform. HEK-293 cells, either expressing the receptor or wild type cells, were loaded with Fluo-3 as follows. Stable HEK-293 clones expressing rat and human MAS receptor or parental cells were plated at a density of 10,000 cells/well in a 96 well plate. On the day of the experiment, the MAS receptor cells were loaded with fluorescent solution (Dulbecco's modified medium with 10% fetal bovine serum containing 4 µM Fluo-3 and 20% pluronic acid). The cells were incubated at 37° C. for one hour in a humidified chamber. Following the incubation step, cells were washed five times in Hanks' with 20 mM Hepes and 0.1% BSA (pH 7.4). The cells were analyzed using the FLIPR system to measure the mobilization of intracellular calcium in response to different compounds.

2) Binding Assay
Membranes of HEK-293 cells, either expressing the receptor or wild type cells were prepared as previously described and frozen at −80° C. On the day of the experiment membranes were homogenized in a buffer containing 50 mM TRIS/HCl ph 7.4, 5 mM MgCl2, EDTA 2 mM, PMSF 0.1 mM, BSA 1 mg/ml using a B Dounce homogenizer and incubated 1 hour at room temperature with different concentrations of $^{125}$I-Dynorphin A-NH2 and with (non-specific binding) or without (specific binding) 1 µM of non-labelled Dynorphin A-NH2. The $^{125}$I-Dynorphin A-NH2 bound was collected by filtration through Whatman GF/B filters presoaked in PEI. The filters were rinsed three times with 2.5 ml of the cold Tris/MgCl$_2$ buffer and then counted using a TopCount NXT (Packard). Protein was measured using a Bio-Rad dye reagent.

II. Results
1) FLIPR Results
HEK-293 cells endogenously express some GPCRs such as bradykinin and PACAP receptors which can be used as internal controls for assays. The background signal was established with all of the compounds in the parental HEK-293 cells (non-transfected) using the FLIPR assay. HEK-293 cells expressing the clone MAS receptor were stimulated with all compounds and calcium responses were compared with those in parental HEK-293 cells. Three compounds, (Dynorphin A, Dynorphin A-NH2 and Dynorphin A 1-13), consistently elicited signals in the transformed cells but not in the wild type cells. This indicates that Dynorphin A and its analogues are interacting with the recombinantly expressed receptors. Confirmation of this conclusion was obtained by the observation of a dose-response relationship with Dynorphin A and its analogues in the cells transfected with MAS receptor, but not in the non-transfected cells or in cells transfected with other orphan receptors. Thus, it has been established that clone rat and human MAS receptor are specific receptors Dynorphin A and its analogues. The rat and human MAS receptors can be used to screen compounds which either mimic the action of Dynorphin A and its analogues (agonists) or antagonize the action of Dynorphin A and its analogues (antagonists).

Screening assays can be performed using the FLIPR assay described above.

2) Binding Results
HEK 293S membranes expressing the cloned MAS receptor showed specific binding for 125I-Dynorphin A-NH2 No specific binding was observed in untransfected HEK 293S membranes.

Screening assays can be performed using binding assay described above. Other assays that can be used include the GTPase assay, adenylyl cyclase assays, assays measuring inositol phosphates, and reporter gene assays (e.g., those utilizing luciferase, aqueorin, alkaline phosphatase, etc.).

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

The invention claimed is:

1. A method for identifying a compound that is able to bind to the rat or human MAS receptor, comprising:
   a) providing a cell or membrane from a cell transformed with a heterologous rat or human MAS receptor gene, said cell expressing the rat or human MAS receptor;
   b) incubating the cell or membrane with Dynorphin A or Dynorphin A-amide or Dynorphin A 1-13 in the presence and absence of a test compound; and
   c) determining binding of Dynorphin A or Dynorphin A-amide or Dynorphin A 1-13 to the cell or membrane, wherein a decrease in binding in the presence of the compound as compared with binding in the absence or the compound indicates that the compound is able to bind to the rat or human MAS receptor.

2. The method of claim 1, wherein the Dynorphin A or Dynorphin A-amide or Dynorphin A 1-13 or the test compound is radioactively labeled.

3. The method of claim 1, wherein the Dynorphin A or Dynorphin A-amide or Dynorphin A 1-13 or the test compound is joined to an enzyme.

4. A method for identifying a compound that increases or decreases the activity of the rat or human MAS receptor, comprising:
   a) providing a cell or membrane from a cell transformed with a heterologous rat or human MAS receptor gene, said cell expressing the rat or human MAS receptor;
   b) incubating the cell or membrane with Dynorphin A or Dynorphin A-amide or Dynorphin A 1-13, and a test compound;
   c) determining intracellular concentration of calcium of said cell; and
   d) comparing the results obtained in step c) with the results obtained with a control in the absence or said test compound;
   wherein a change in intracellular concentration of calcium of said cell in the presence of said compound as compared with intracellular concentration of calcium of said cell in the absence of said compound indicates that said compound increases or decreases MAS receptor activity.

* * * * *

UNITED STATES PATENT AND TRADEMARK OFFICE
CERTIFICATE OF CORRECTION

PATENT NO. : 7,078,177 B2
APPLICATION NO. : 10/250629
DATED : July 18, 2006
INVENTOR(S) : Ahmad et al.

It is certified that error appears in the above-identified patent and that said Letters Patent is hereby corrected as shown below:

Col. 8, line 32, claim 4, replace "or" with -- of --.

Signed and Sealed this

Nineteenth Day of December, 2006

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 17
<212> TYPE: PRT
<213> ORGANISM: artificial
<220> FEATURE:
<223> OTHER INFORMATION: synthetic peptide

<400> SEQUENCE: 1

Tyr Gly Gly Phe Leu Arg Arg Ile Arg Pro Lys Leu Lys Trp Asp Asn
1               5                   10                  15

Gln
```